US008628625B2

(12) United States Patent
Witten

(10) Patent No.: US 8,628,625 B2
(45) Date of Patent: Jan. 14, 2014

(54) METHOD OF DETECTION/EXTRACTION, AND RELATED DETECTION/EXTRACTION DEVICE

(76) Inventor: Mark L. Witten, Tucson, AZ (US)

( * ) Notice: Subject to any disclaimer, the term of this patent is extended or adjusted under 35 U.S.C. 154(b) by 710 days.

(21) Appl. No.: 12/681,035

(22) PCT Filed: Oct. 1, 2007

(86) PCT No.: PCT/US2007/080101

§ 371 (c)(1), (2), (4) Date: Mar. 31, 2010

(87) PCT Pub. No.: WO2009/045208

PCT Pub. Date: Apr. 9, 2009

(65) Prior Publication Data

US 2010/0216118 A1 Aug. 26, 2010

(51) Int. Cl.
*B08B 7/04* (2006.01)

(52) U.S. Cl.
USPC .............. 134/18; 134/26; 134/10; 134/22.14; 134/34

(58) Field of Classification Search
USPC ............................... 134/18, 26, 10, 22.14, 34
See application file for complete search history.

(56) References Cited

U.S. PATENT DOCUMENTS 5,114,579 A 5/1992 Takigawa
5,156,810 A * 10/1992 Ribi ........................... 422/82.01
5,679,254 A * 10/1997 Chakrabarti .................. 210/642
5,840,527 A * 11/1998 Schilling et al. ............. 435/69.1
5,945,026 A 8/1999 Thames
6,200,943 B1 3/2001 Romack et al.
2005/0079131 A1 * 4/2005 Lanza et al. ................. 424/1.11

FOREIGN PATENT DOCUMENTS

WO WO 2009/045208 A1 4/2009

OTHER PUBLICATIONS

Sisson et al. "Synthetic ion channels and pores (2004-2005)", Chem. Soc. Rev., 2006, 35, 1269-1286. First Published May 18, 2006.

L. Powers and P.S. Pershan, Division of Applied Sciences, Harvard University, Cambridge, MA 02138 USA. "Monodomain Samples of Dipalmitoyl Phosphatidylcholine with varying concentrations of water and other ingredients." Biophysical Journal. vol. 20. 1977. pp. 137-152.

Harishchandra, Rakesh Kumar et al. "The effect of compatible solute ectoines on the structural organization of lipid monolayer and bilayer membranes." Biophysical Chemistry. pp. 2-15. www.sciencediret.com.

Dong, Qun et al. "Degradation of surfactant protein D by alveolar macrophages." AJP—Lung Cellular and Molecular Physiology. vol. 574, Issue 1, L97-L105, Jan. 1998. pp. 1-19.

Cubillos, Maria et al. "Lipid Peroxidation Rates of DPPC Liposomes Containing Different Amounts of Oxidable Lipids Show Opposite Dependence with the Temperature." Journal of the Chilean Chemical Society. vol. 51, No. 1, Mar. 2006. pp. 1-5.

* cited by examiner

*Primary Examiner* — Chester Barry

(57) ABSTRACT

A method that uses an L-α-dipalmitoleoyl-phosphatidylcholine (DPPC) surfactant based device that reacts with a substance in a known manner, to detect a substance of interest or to extract a substance of interest from a material is provided. The principles of the present invention are particularly useful in detecting/measuring a substance that is harmful to a human, and also to extracting NACL from saltwater.

19 Claims, 5 Drawing Sheets

METHOD OF DETECTION/EXTRACTION, AND RELATED DETECTION/EXTRACTION DEVICE

GOVERNMENT RIGHTS

This invention was made with government support under Research grant F49620-00-0119 awarded by the United States Air Force Office of Scientific Research. The government has certain rights in the invention.

RELATED APPLICATION/CLAIM OF PRIORITY

This application is a national stage application under 35 U.S.C. §371 of, and claims priority from, International Application No. PCT/U52007/080101, filed 1 Oct. 2007, which is herein incorporated by reference in its entirety.

BACKGROUND

The present invention relates to a new and useful method for using an L-α-dipalmitoleoyl-phosphatidylcholine (DPPC) based surfactant to detect materials of interest (e.g. materials that can be harmful to a human being), and to extract materials of interest from a material (e.g. extracting NACL from saltwater), and to a detection/extraction device that can be used in such methods.

Pulmonary inhalation of aerosolized particles, either chemical or biological in origin, is one of the most direct forms of exposure to environmental pollutants and biochemical or biological warfare agents. However, the lungs of asthmatics also produce nitric oxide gas which may be used as a treatment guide for chronic asthma patients. Smith, et al., (2005) *New Engl. J. Med.* 352:2163. Furthermore, ethane gas is being utilized as a biomarker for the degree of severity of interstitial lung disease in patients. Kanoh, et al., (2005) *Chest* 128:2387. There are many occupational settings in which workers are exposed to high jet fuel levels such as aircraft refueling crews, aircraft mechanics, and pilots. Bell, et al., (2005) *Aviat. Space Environ. Med.* 76:1136. Additionally, the threat of chemical and biological warfare agent exposure via inhalation presents a potentially serious health and security threat to the United States. Hendrickson and Hedges (2005) *Crit. Care Clin.* 21:641. Thus, there is a continuing need in the art to develop devices capable of detecting, and preferably measuring the concentrations of these and other toxic compounds.

However, the development of nanometer-sized bioanalytical devices has been wide-ranging and rapid, bridging the gap between material technology and the biochemical and physical structures of living organisms. Applicable to this study are the immobilization of lipid membranes to serve as biological sensing elements. Recently, methods have been developed that utilize ellipsometry (Puu and Gustafson, 1997), atomic force microscopy (Fisher and Tjarnhage, 2000), and fluorescence (Brooks at al., 2000) to investigate and monitor nanometer thick lipid film phenomena. Additionally, the deposition and lifetime of lipid films on oxide and mica templates have been improved allowing for the utilization of these membranes in a variety of biosensor applications (Benga and Tager, 1988; Csucs and Ramsden, 1998; Kossek et al., 1998; Notter, 2000; Sackman 1996). These developments, coupled with a better understanding of phospholipid physiology in the lung (Gennis, 1989; Harrison and Lung, 1980; Smondyrev and Berkowitz, 1999; Walters et al., 2000; Yao et al., 1994), have made the prospect of a lipid biosensor feasible.

SUMMARY OF THE INVENTION

The present invention provides a method that uses an L-α-dipalmitoleoyl-phosphatidylcholine (DPPC) surfactant based device that reacts with a substance in a known manner, to detect a substance of interest or to extract a substance of interest from a material. The principles of the present invention are particularly useful in detecting/measuring a substance that is harmful to a human, and also to extracting NACL from saltwater.

In its preferred form, the invention provides a DPPC surfactant-based biofilm, whose configuration can be designed to (a) detect and/or measure the presence and/or concentration of the harmful substance, by the change in shape of the biofilm when exposed to the substance, or to (b) extract NaCl from saltwater.

In a method according to the present invention, a sensor with the L-α-dipalmitoleoyl-phosphatidylcholine (DPPC) surfactant based biofilm is exposed to a fluid (e.g. an aerosol, vapor, or combination of aerosol and vapor) containing the substance, and is used to detect or measure the concentration of the substance. The DPPC surfactant based biofilm has been found to change shape (i.e. it changes thickness in a characteristic way) when exposed to a fluid containing the substance, and by analyzing the shape of the biofilm, e.g. with a white light measuring system, characteristic changes in the shape of the DPPC surfactant based biofilm can be used to detect the presence of, or measure the concentration of, the substance in the fluid.

In a method of reacting a substance with a surfactant based biofilm, according to the principles of the present invention, a reactive device is provided, that comprises a substrate with a DPPC surfactant based biofilm that is known to react with a substance in the predetermined manner when the DPPC surfactant based biofilm is exposed to the substance. The DPPC surfactant based biofilm is exposed to the substance to enable the reaction with the substance to occur in the predetermined manner. When the biofilm is used as a sensor/detector, the effect on the biofilm is then determined to identify the presence and/or concentration of the substance. When the biofilm is used to extract a substance (e.g. to extract NACL from saltwater), the substance will have adhered to the biofilm to extract the substance.

Whether the method involves detection or measurement of the substance, or extraction of the substance, the DPPC surfactant based biofilm is generally exposed to a fluid containing the substance to produce the reaction.

When the method involves detection or measurement of the substance, the DPPC surfactant based biofilm is characterized in that it has a predetermined thickness when not exposed to the substance and changes thickness in a predetermined manner when exposed to the substance. Moreover, the change in thickness of the biofilm can also be a measure of the concentration of the substance in a fluid. A particularly useful feature of a detection process using a biofilm based on a DPPC surfactant is that with most substances of interest the biofilm will not only change thickness, in a characteristic way, depending on the substance being detected, and when the substance is removed from the environment of the biofilm, the biofilm will return to its original thickness, so that the substrate can be reused to detect the substance. Of the substances with which the biofilm of the present invention is designed to function as a detector, to date only ethanol has been found to change the biofilm in a manner that is not recovered when the ethanol is removed from the environment of the biofilm.

When the biofilm is being used to detect or measure the substance, the DPPC surfactant-based biofilm preferably has a thickness of about 200 Angstroms when not exposed to the substance. When the biofilm is being used to extract NaCl from saltwater, the DPPC surfactant-based biofilm preferably has a thickness of about 300 Angstroms.

In one of its important detection/measurement aspects, the DPPC surfactant based biofilm is designed to react in a predetermined manner when exposed to organic particles in the fluid to produce the reaction. More specifically, the DPPC surfactant based biofilm is designed to react in the predetermined manner when exposed to a fluid containing a hydrocarbon that is harmful to a human lung to produce the reaction. In addition, the DPPC surfactant based biofilm in a 200 Angstrom thickness has a sensitivity such that it will react in the predetermined manner when exposed to a ten-billionth of a gram of a hydrocarbon that is harmful to a human lung.

Another important detection aspect of the DPPC surfactant based biofilm of the present invention is that it will react in the predetermined manner when the DPPC surfactant based biofilm is exposed to a fluid containing the hydrocarbon to produce the reaction. The surfactant based biofilm has a thickness of about 200 Angstroms when not exposed to the hydrocarbon.

Still another important detection aspect of the DPPC surfactant based biofilm of the present invention is that in the 200 Angstrom thickness it will react in the predetermined manner, when the surfactant based biofilm is exposed to a fluid with a hydrocarbon fuel (e.g. jet fuel, S-8 synthetic jet fuel, gasoline, diesel, kerosene, or combinations thereof) to produce the reaction.

Yet another important detection aspect of the DPPC surfactant based biofilm of the present invention is that in the 200 Angstrom thickness it will react in the predetermined manner, when the surfactant based biofilm is exposed to a fluid containing a biological and/or chemical warfare agent (e.g. ricin, sarin, anthrax, phosgene gas, mustard gas, etc).

Still another important detection aspect of the DPPC surfactant based biofilm of the present invention is that in the 200 Angstrom thickness it will react in the predetermined manner, when the surfactant based biofilm is exposed to a fluid containing a hydrocarbon-based solvent (e.g. acetone, methanol, ethanol, or combinations thereof) to produce the reaction.

Yet another important detection aspect of the DPPC surfactant based biofilm of the present invention is that in the 200 Angstrom thickness it will react in the predetermined manner, when the surfactant based biofilm is exposed to a gas containing nitric oxide, carbon dioxide or methane to produce the reaction. Such gas or gases are generally emitted from asthmatic patients or patients suffering from other pulmonary diseases.

Still another important detection aspect of the DPPC surfactant based biofilm of the present invention is that in the 200 Angstrom thickness it will react in the predetermined manner, when the surfactant based biofilm is exposed to an airborne metal that includes tungsten, arsenic and/or cobalt to produce the reaction.

Still another important detection aspect of the DPPC surfactant based biofilm of the present invention is that in the 200 Angstrom thickness it will react in the predetermined manner, when the surfactant based biofilm is exposed to a fluid that contains a radioactive material (e.g. technetium-labelled diethylenetriamine pentaacetate (99mTc-DTPA)).

Yet another important detection aspect of the DPPC surfactant based biofilm of the present invention is that in the 200 Angstrom thickness it will react in the predetermined manner, when the surfactant based biofilm is exposed to a fluid that contains a virus such as A/Hong Kong/8/68 influenza virus.

Still another important concept of the DPPC surfactant-based biofilm of the present invention is that in a 300 Angstrom thickness it will react in the predetermined manner, when the DPPC surfactant-based biofilm is exposed to saltwater and is used to extract NaCl from the saltwater.

Moreover, when used to extract NaCl from saltwater, applicant has determined that the reaction of the DPPC surfactant-based biofilm with saltwater works best when the surfactant-based biofilm includes salmon sperm DNA.

Other features of the present invention will become further apparent from the following detailed description and the accompanying drawings.

DETAILED DESCRIPTION

Figure 1B:
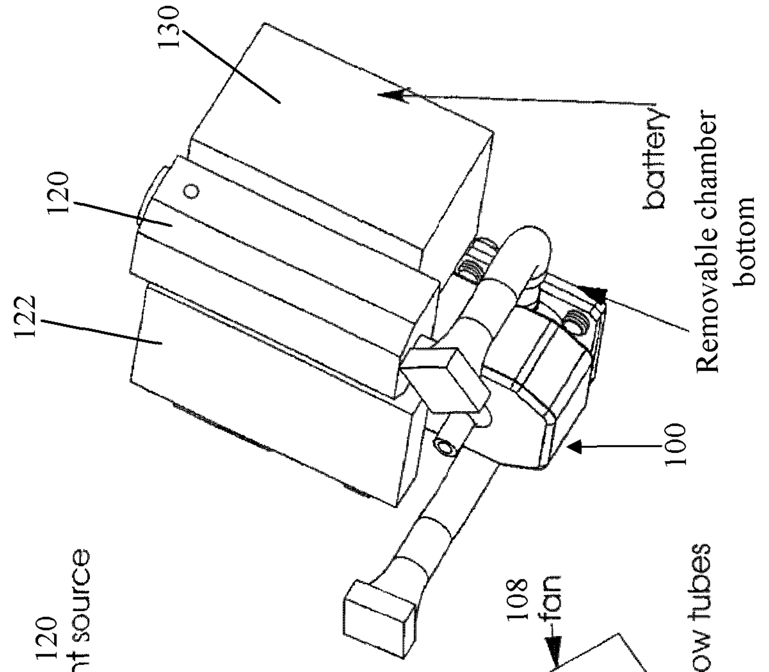
FIGS. 1*a* and 1*b* are schematic illustrations of a system with a DPPC chemical sensor device, according to the principles of the present invention, and designed to practice a detection method according to the principles of the present invention.
Figure 1A:
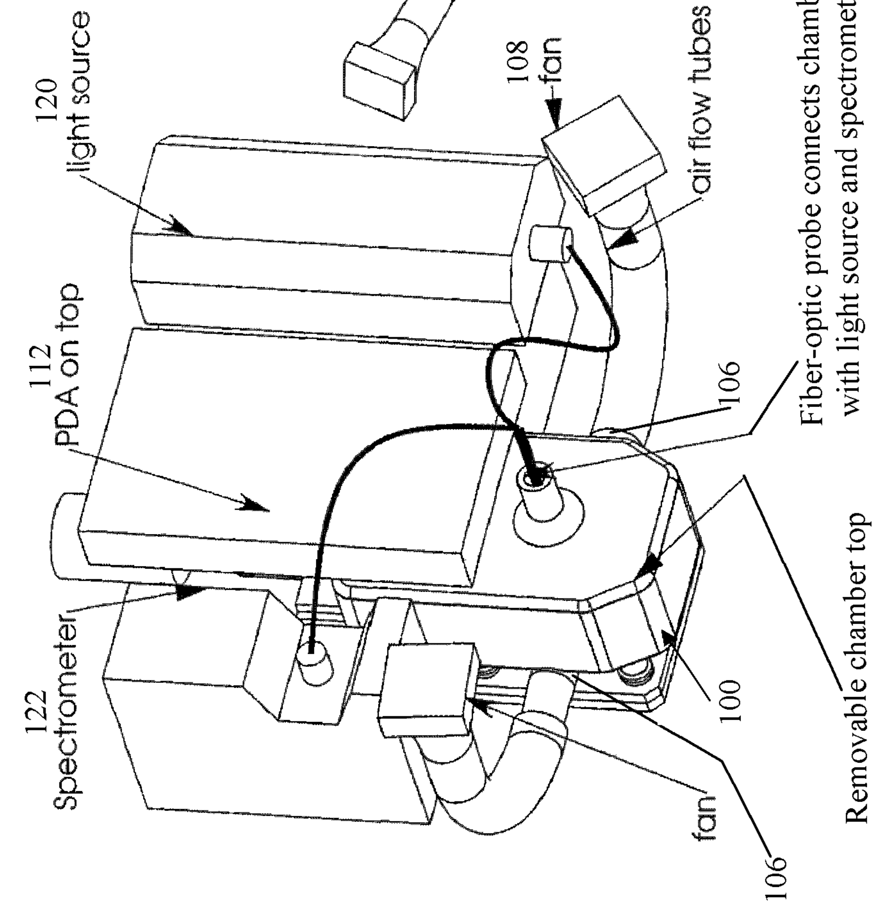
Figures 2A, 2B:
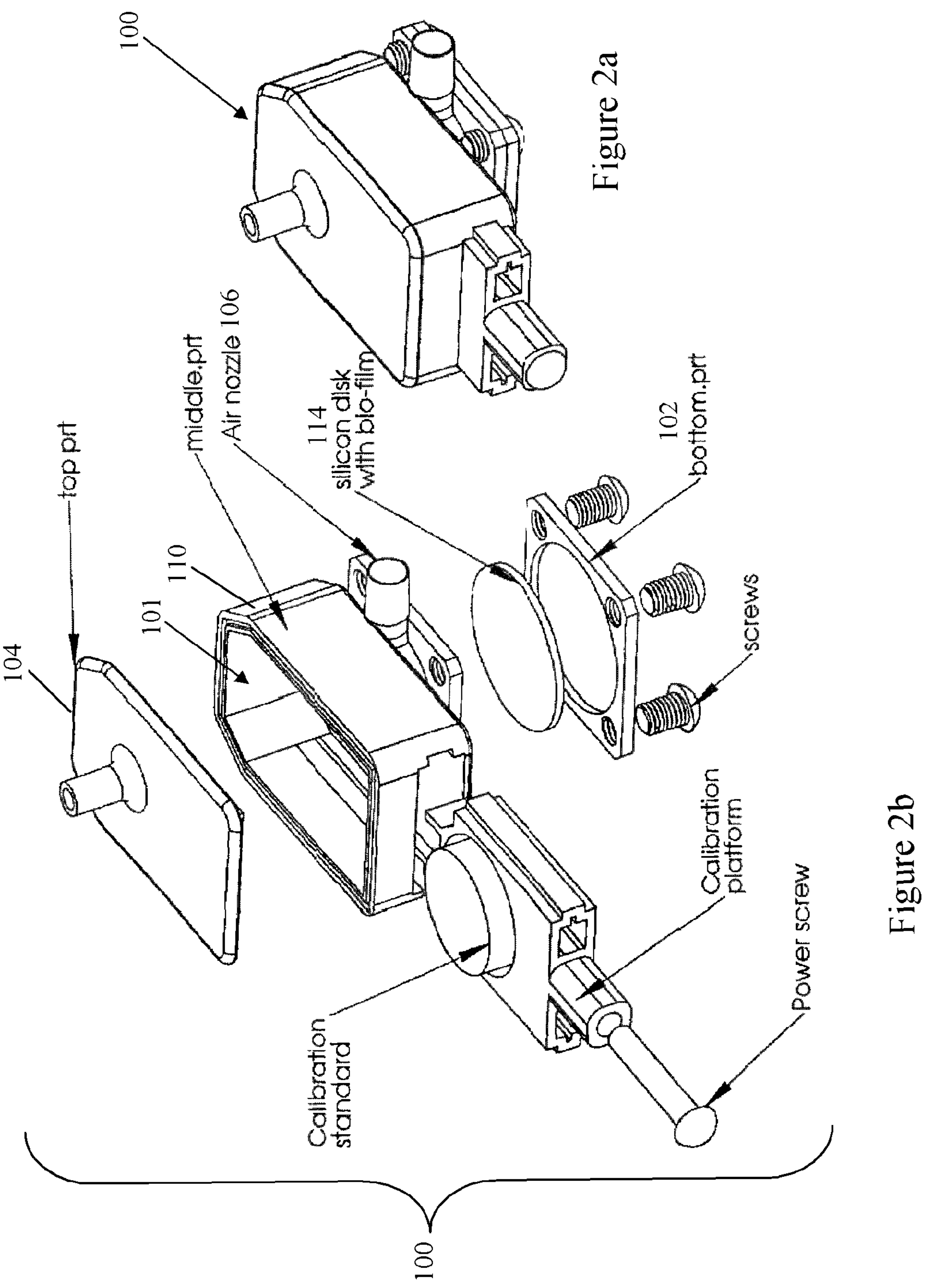
FIG. 2*a* is a schematic illustration of the detection/measurement chamber.
FIG. 2*b* is an exploded schematic illustration of the components of the detection/measurement chamber, that includes the detection/measurement device of the present invention, and which can be used in the practice of the method of the present invention.
Figure 3:
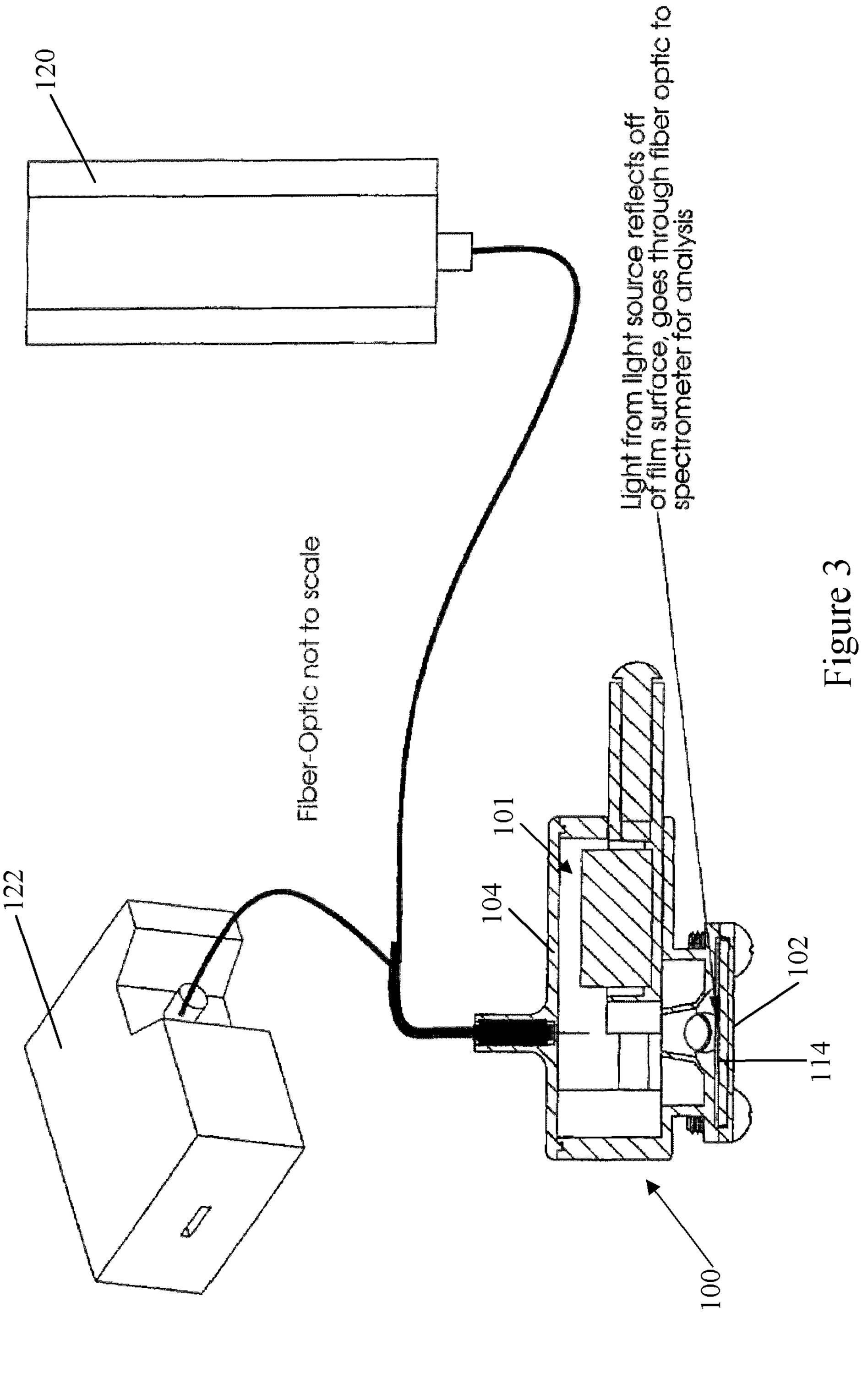
FIG. 3 is a schematic illustration of the light pathway schematic of the detection/measurement system that includes the detection/measurement device of the present invention, and that can be used in the practice of the method of the present invention.
Figure 4:
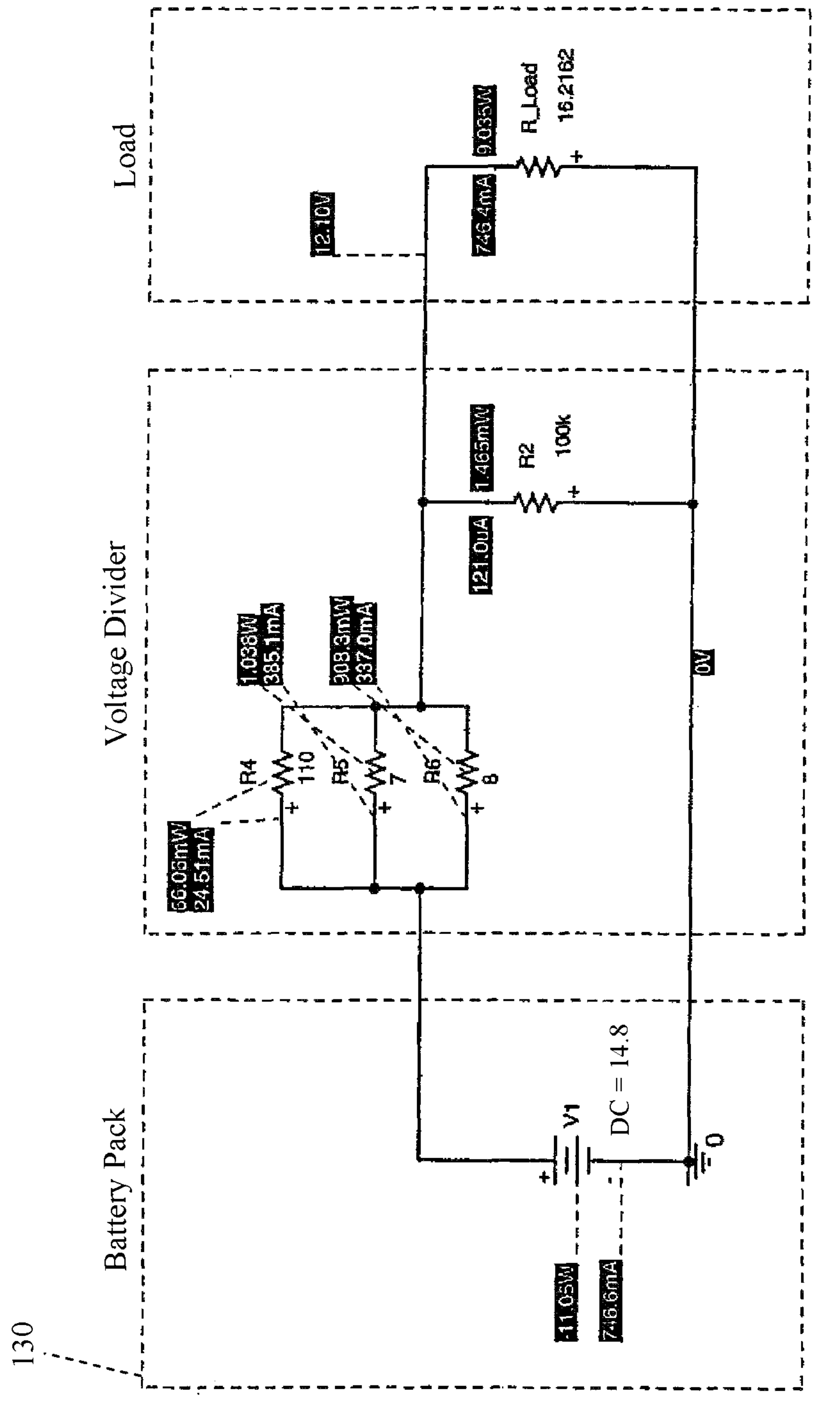
FIG. 4 shows the electrical wiring diagram of the detection/measurement system that can be used in the practice of the method of the present invention.

As discussed above, the present invention relates to a new and useful sensor and method for detecting and/or measuring a substance, or for extracting a substance from a material, using a DPPC surfactant-based material, DPPC is a thermally stable phospholipid component of lung surfactant (and is referred to herein as a DPPC surfactant). The DPPC surfactant-based material is preferably a DPPC surfactant-based biofilm that is applied to a substrate (e.g. a silicon and/or stainless steel substrate). The principles of the invention are described below in connection with a sensor and method originally developed for detecting jet fuel, and from those principles, the manner in which the principles of the present invention can be used in detecting/measuring various other substances, and in extracting NaCl from saltwater will be explained in a way that will make them clear to those in the art.

Initially, it is believed that the manner in which the validity of an L-α-dipalmitoleoyl-phosphatidylcholine (DPPC) surfactant based biosensor has been developed will be useful to those in the art. A DPPC surfactant biofilm was initially developed for detecting hydrocarbon and organic agent presence in a fluid sample. The DPPC surfactant based biofilm was created from a 25 mg/ml solution of DPPC in acetone/chloroform (1:1, vol:vol) and applied to silicon wafers 5.08 cm diameter) with 5700 Angstrom thermally grown silicon dioxide substrate. A wafer spinning apparatus (a Solitec photo resist spin coater, by Solitec Wafer Processing, Inc., San Jose, Calif.) was used in the preparation of the biofilm. About 0.25 ml of the DPPC solution was deposited on the center of the wafer, and the wafer spun to produce a DPPC film of uniform thickness (900-1200 Angstroms) on a 5700 Angstrom silicon dioxide wafer. The DPPC film was stored in a Class PM-100 clean room for 48 hours prior to use to allow the chloroform and acetone to evaporate completely.

The apparatus shown in FIGS. 1*a*, 1*b*, 2*a*, 2*b*, 3 and 4 was then used to analyze certain test substances to determine the capabilities of the DPPC film. The apparatus included a cylindrical exposure chamber 101 that was 2.20 cm in diameter and 5.00 cm deep. An aluminum plate 102 was attached to the bottom of the chamber using standard screws and a rubber o-ring to create an air-tight seal. A removable 0.635 cm thick transparent glass plate 104 was then affixed to the topside of the chamber using silicon vacuum grease as a sealant. The chamber's volume was about 73.98 $cm^2$. Two 0.635 cm National Pipe Thread (NPT) holes 106 were positioned at 90 and 270 degrees opposite each other through the central column in the block 110 that forms the housing of the chamber, which served as inlet and outlet holes for organic compound saturated $N_2$ flows. A fan 108 was used to control the flow of fluid (air) through the chamber 100. A light source 120 produced white light in the 400 nm to 850 nm range. The DPPC film optical thickness changes were measured with a Filmetrics model F20 spectrometer 122 (made by Filmetrics, Inc., San Diego, Calif.). A PDA 112 provided a user interface. The circuit shown in FIG. 4 was powered by a battery 130 used to control the air fan 108, the light source 120, and the PDA 112. Film thickness was determined by measuring interference between incident and reflected light through the DPPC film/silicon dioxide substrate film layers. The resulting data was used by the Filmetrics software to compute the total optical thickness of the DPPC film and silicon dioxide substrate. The DPPC film thickness was then calculated by taking the difference between the total thickness of the DPPC film and substrate and the 5700 Angstrom thick substrate.

A panel of three flowmeters were provided to control $N_2$ flow rates. Two $N_2$ flows comprised the exposure component of the apparatus. Each was regulated by a separate rate-adjustable flow meter. One of these nitrogen flows cycled 100% pure $N_2$ through the liquid exposure compound in a bubbler to create a test compound saturated $N_2$ flow. The other 100% pure $N_2$ flow served to dilute the test compound saturated nitrogen flow. Additionally, the third nitrogen flow was 100% pure $N_2$ controlled by the final rate-adjustable flow meter, which was used to purge the chamber of test compound saturated $N_2$ during recovery periods.

The apparatus was modified to expose the DPPC surfactant based biofilm to two test compounds simultaneously. This set-up allowed for simultaneous JP-8 jet fuel and saline (0.85% sodium chloride, 99.15% water) exposure, simulating a JP-8 jet fuel response in the internal lung environment. In this trial, the one test compound set-up described above, was modified as follows: the third purging/recovery pure $N_2$ flow was saturated with saline (0.85% sodium chloride, 99.15% water) after cycling through a saline (0.85% sodium chloride; 99.15% water) bubbler. This set-up allowed for a saline saturated environment during exposure and recovery periods. Both the single test compound exposure and modified JP-8 jet fuel/saline solution exposure apparatus were based on the apparatus shown in FIGS. 1*a*, 1*b*, 2*a*, 2*b*, 3 and 4.

The standard protocol for DPPC film exposure to test compounds consisted of a five-minute test compound saturated $N_2$ flows exposure. The recovery nitrogen flow purged the chamber for two minutes immediately following the exposure period. This process was repeated three times to demonstrate the reproducibility of a thickness response for the DPPC film. Thickness data were obtained every 15 seconds throughout the three exposure and recovery periods.

Test compound control data involved a silicon dioxide wafer without DPPC film exposed to a test compound saturated $N_2$ flow. The purpose of these experiments was to determine if the test compound saturated $N_2$ flow altered the spectrophotometer's thickness determination independent of the DPPC film's optical thickness change. Six trials were performed for each test-agent using five-minute exposure periods and two-minute recovery periods as the standard control protocol.

The DPPC surfactant based biofilm's response to organic compounds was detected using a 400-850 nm light Filmetrics spectrophotometer. DPPC film were exposed to nitrogen flows saturated with the following test compounds: JP-8 jet fuel, semiconductor grade acetone, saline solution (0.85% sodium chloride, 99.15% water), and ultra-pure deionized water. The DPPC film's exposure response was characterized by a change in optical thickness. Saline produced a mean thickness change of 190.4 (19.0) Å (n=6). Semi-conductor grade acetone produced a mean thickness change of 172.9 (38.4) Å (n=6). JP-8 jet fuel produced a mean thickness change of 68.8 (17.5) Å (n=6). Ultra-pure de-ionized water produced a mean thickness change of 186.8 (10.7) Å (n=6). Additionally, simultaneous saline and JP-8 jet fuel exposure produced a thickness change of 83.5 (0.9) Å (n=10) greater than saline exposure alone. From this preliminary study, Applicant determined that the DPPC film response to test compound exposure was measurable, using the 400-850 nm light spectrophotometer. This method was robust and repeatable. This technique was capable of measuring a wide-range of test compounds. This technique demonstrated specificity in detecting JP-8 jet fuel exposure in a saline-saturated simulated lung environment.

Moreover, the study demonstrated that the DPPC based surfactant biofilm's response to test agent exposure, in the form of an optical thickness increase, was measurable using the light spectrophotometer. This apparatus was both nanometer sensitive to low concentrations and rapid. The attached Table 1 further shows the results of the study.

The foregoing study produced a successful biosensor in that it was rapid, reusable, nanometer sensitive, and detected different test agents. Of particular interest was the film's response when simultaneously exposed to JP-8 jet fuel and saline saturated $N_2$ flow. The DPPC film's increase in optical thickness of 83.5 (0.9) Å to the test compound mixture demonstrates that an observable film response to JP-8 is measurable in a simulated lung environment. The sensitivity of the test device was determined to be a ten-thousandth of a gram for a biofilm thickness of 900-1200 Angstrom thickness. Based on the study, applicant concluded that a biofilm sensor, of the type utilized in the study, and a detection system build along the principles of the system of FIGS. 1*a*, 1*b*, 2*a*, 2*b*, 3 and 4, would have great utility detection of various substances, e.g. chemical and biological warfare agents, hydrocarbons, and environmental pollutants, etc.

Thus, a detection system has been developed where the DPPC surfactant based biofilm can be exposed to a substance of interest (that is contained in a fluid sample) and used to detect the substance of interest. The detection system utilizes a DPPC surfactant based biofilm on a substrate, and is useful in detecting the presence of a substance of interest in a fluid sample.

As a result of further research following the preliminary study, applicant determined that a DPPC surfactant based biofilm, in a thickness of 200 Angstroms, could to used, in a system constructed in accordance with the principles of the system shown in FIGS. 1*a*, 1*b*, 2*a*, 2*b*, 3 and 4 (and described above), would be effective to detect a number of substances of interest and also to measure the concentrations of a number of substances.

Currently, a DPPC surfactant based biofilm is prepared in the following manner. A disc (e.g. silicon with a silicon dioxide substrate having a thickness of close to 200 Angstroms) is initially cleaned with ethanol spray, and wiped clean with Kim Wipes. Then, acetone (e.g. about 1 ml.) is added to a container of DPPC (about 0.25 mg/ml of DPPC), and chloroform (e.g. about 1 ml) is added to the DPPC/acetone solution. Then, the addition of acetone, followed by chloroform, to the DPPC solution is repeated. The disc (substrate), is then placed on a spinner disposed in a vacuum chamber, a vacuum is drawn in the chamber, and the disc (substrate) is spun in the vacuum chamber. The spinner speeds may vary, depending on the thickness of the biofilm layer desired, in accordance with the following criteria: 1500 rpm for a thickness of 500 Angstroms; 2000 rpm for a thickness of 400 Angstroms; 2500 rpm for a thickness of 300 Angstroms; 3000 rpm for a thickness of 200 Angstroms (it should be noted that the preferred thickness of the biofilm when used to detect or measure a substance, is about 200 Angstrom thickness). The speed of the spinner may be adjusted while the substrate is spinning. Once the spinning speed of the substrate is determined, approximately 0.5 ml of the DPPC/acetone/chloroform solution described above is puddled on the center of the substrate, and the substrate spun for about 10 seconds. The puddle should be approximately circular and cover an area about the size of a quarter. The substrate is then examined for irregularities in the biofilm. If irregularities exist (the biofilm on the substrate should be regular for a radius of about 0.5 cm in the center of the substrate), the substrate is spun and rinsed with acetone to clean the substrate. When the substrate has the desired biofilm thickness and quality, the vacuum is turned off and the substrate with the DPPC surfactant based biofilm is removed from the spinner.

In a method according to the present invention, a sensor with the L-α-dipalmitoleoyl-phosphatidylcholine (DPPC) surfactant based biofilm is exposed to an aerosol or vapor containing the substance, and is used to detect or measure the concentration of the substance. The DPPC surfactant based biofilm has been found to change shape (i.e. it changes thickness in a characteristic way) when exposed to an aerosol or vapor containing the substance, and by analyzing the shape of the biofilm, e.g. with a white light measuring system, characteristic changes in the shape of the DPPC surfactant based biofilm can be used to detect the presence of, or measure the concentration of, the substance in the vapor or aerosol.

In a method of reacting a substance with a surfactant based biofilm, according to the principles of the present invention, a reactive device is provided, that comprises a substrate with a DPPC surfactant based biofilm that is known to react with a substance in the predetermined manner when the DPPC surfactant based biofilm is exposed to the substance. The DPPC surfactant based biofilm is exposed to the substance to enable the reaction with the substance to occur in the predetermined manner, and the effect on the biofilm is then determined to identify the presence and/or concentration of the substance.

Whether the method involves detection or measurement of the substance, or removal of the substance, the DPPC surfactant based biofilm is generally exposed to a fluid (aerosol, vapor, or combination of aerosol and vapor) containing the substance to produce the reaction.

When the method involves detection or measurement of the substance, the DPPC surfactant based biofilm is characterized in that it has a predetermined thickness when not exposed to the substance and changes thickness in a predetermined manner when exposed to the substance. A particularly useful feature of a detection process using a biofilm based on a DPPC surfactant is that with most substances of interest the biofilm will not only change thickness, in a characteristic way, depending on the substance being detected, and when the substance is removed from the environment of the biofilm, the biofilm will return to its original thickness, so that the substrate can be reused to detect the substance. Of the substances tested, to date only ethanol has affected the biofilm in a manner such that the biofilm cannot be reused after it has detected the substance.

When the biofilm is being used to detect or measure the substance, the DPPC surfactant-based biofilm preferably has a thickness a about 200 Angstroms when not exposed to the substance. When the biofilm is being used to extract NaCl from saltwater, the DPPC surfactant-based biofilm preferably has a thickness of about 300 Angstroms.

In one of its important detection/measurement aspects, the DPPC surfactant based biofilm is designed to react in a predetermined manner when exposed to organic particles in the fluid to produce the reaction. More specifically, the DPPC surfactant based biofilm is designed to react in the predetermined manner when exposed to a fluid containing a hydrocarbon that is harmful to a human lung to produce the reaction. In addition, the DPPC surfactant based biofilm in a 200 Angstrom thickness has a sensitivity such that in airborne metals it will react in the predetermined manner when exposed to a ten-billionth of a gram of an airborne metal that is harmful to a human lung. Still further, the DPPC surfactant based biofilm has been determined to have a sensitivity of less than 70 parts per million when exposed to jet fuel.

Another important detection aspect of the DPPC surfactant based biofilm of the present invention is that it will react in the predetermined manner, when the DPPC surfactant based biofilm is exposed to a fluid containing the hydrocarbon to produce the reaction. The surfactant based biofilm has a thickness of about 200 Angstroms when not exposed to the hydrocarbon.

Still another important detection aspect of the DPPC surfactant based biofilm of the present invention is that in the 200 Angstrom thickness it will react in the predetermined manner, when the surfactant based biofilm is exposed to a fluid with a hydrocarbon fuel (e.g. jet fuel, S-8 synthetic jet fuel, gasoline, diesel, kerosene, or combinations thereof) to produce the reaction.

Yet another important detection aspect of the DPPC surfactant based biofilm of the present invention is that in the 200 Angstrom thickness it will react in the predetermined manner, when the surfactant based biofilm is exposed to a fluid containing a biological and/or chemical warfare agent (e.g. ricin, sarin, anthrax, phosgene gas, mustard gas, etc).

Still another important detection aspect of the DPPC surfactant based biofilm of the present invention is that in the 200 Angstrom thickness it will react in the predetermined manner, when the surfactant based biofilm is exposed to a fluid containing hydrocarbon-based solvent (e.g. acetone, methanol, ethanol, or combinations thereof) to produce the reaction.

Yet another important detection aspect of the DPPC surfactant based biofilm of the present invention is that in the 200 Angstrom thickness it will react in the predetermined manner, when the surfactant based biofilm is exposed to a gas containing nitric oxide, carbon dioxide or methane to produce the reaction. Such gas is generally emitted from asthmatic patients or patients suffering from other pulmonary diseases.

Still another important detection aspect of the DPPC surfactant based biofilm of the present invention is that in the 200 Angstrom thickness it will react in the predetermined manner, when the surfactant based biofilm is exposed to an airborne metal that includes tungsten, arsenic and/or cobalt to produce the reaction.

Still another important detection aspect of the DPPC surfactant based biofilm of the present invention is that in the 200 Angstrom thickness it will react in the predetermined manner, when the surfactant based biofilm is exposed to a fluid that contains a radioactive material (e.g. technetium-labelled diethylenetriamine pentaacetate (99mTc-DTPA)).

Yet another important detection aspect of the DPPC surfactant based biofilm of the present invention is that in the 200 Angstrom thickness it will react in the predetermined manner, when the surfactant based biofilm is exposed to a fluid that contains a virus such as A/Hong Kong/8/68 influenza virus.

Still another important concept of the DPPC surfactant-based biofilm of the present invention is that in a 300 Angstrom thickness it will react in the predetermined manner, when the DPPC surfactant-based biofilm is exposed to saltwater, and will extract NaCl from the saltwater.

Moreover, when used to extract NaCl from saltwater, applicant has determined that the reaction of the DPPC surfactant-based biofilm with saltwater works best when the surfactant-based biofilm includes salmon sperm DNA.

Figure 5:
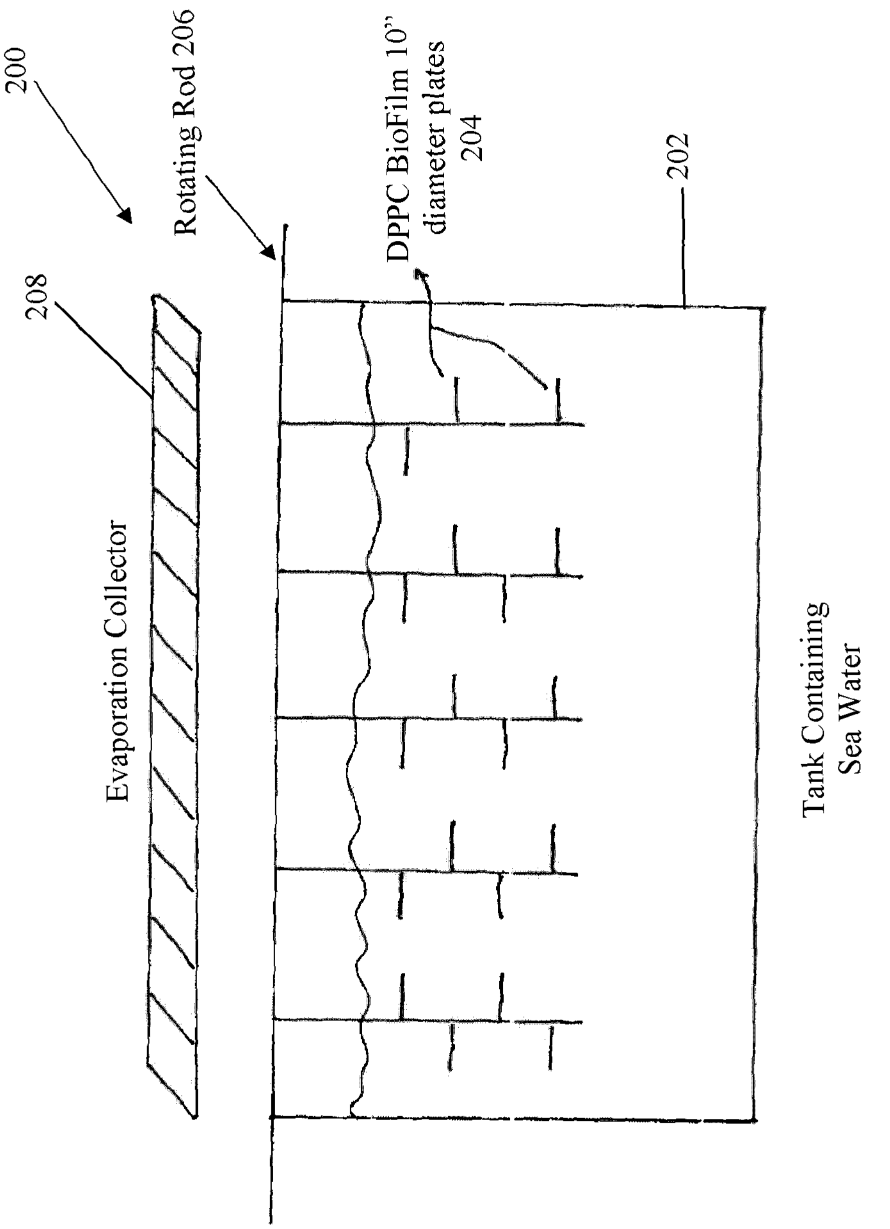
FIG. 5 is a schematic illustration of system components and the manner in which they can be used in a method for extracting NaCL from saltwater, according to the principles of the present invention.

The DPPC surfactant-based biofilm is prepared generally in the manner described above. The DPPC/acetone/chloroform solution is prepared in the manner described above. The salmon sperm DNA (preferably pure salmon sperm DNA) is added to the DPPC/acetone/chlorine solution just prior to its application (by puddling) on the spinner. The salmon sperm DNA is added in an amount that can vary from 0.05 ml to 0.50 ml (0.15 ml is currently preferred). Once the biofilm has been created, in a thickness of about 300 Angstroms, it is used in a system 200 shown schematically in FIG. 5. Specifically, a number of 10 inch diameter plates 204, each with a DPPC surfactant-based biofilm (with salmon sperm DNA) are prepared with the biofilm in a thickness of about 300 Angstroms. The plates 204 are secured to a rotatable support structure 206 that is immersed in a tank 202 of seawater. The tank is preferably operated at a temperature in the range of 28-31 degrees Centigrade, and the support structure 206 rotated (periodically or continuously) to enable the NaCl molecules to adhere to the biofilm. An evaporation collector 208 is also provided. The foregoing structure will cause a significant amount of NaCl to adhere to the plates 204, which can be periodically removed and replaced to enable more NaCl to be removed from the saltwater.

With the foregoing disclosure in mind, it is believed that various adaptations of the use of an L-α-dipalmitoleoyl-phosphatidylcholine (DPPC) surfactant based device and method that reacts with a substance in a known manner, to detect a substance of interest or to extract a substance of interest from a material, will be apparent to those in the art.

The invention claimed is:

1. A method of reacting a substance with a surfactant-based biofilm, in an environment outside a human body comprising (a) providing a reactive structure located in an environment outside a human body comprising a substrate with a surfactant-based biofilm that is known to react with a substance in a predetermined manner when the surfactant-based biofilm is exposed to the substance, the surfactant-based biofilm comprising a DPPC surfactant-based biofilm; and (b) exposing the surfactant-based biofilm to the substance in an environment outside a human body to produce the reaction with the substance in the predetermined manner.

2. The method of claim 1, wherein the surfactant-based biofilm is exposed to a fluid containing the substance in an environment outside a human body to produce the reaction.

3. The method of claim 2, wherein the surfactant-based biofilm is characterized in that it has a predetermined thickness when not exposed to the substance in an environment outside a human body and changes thickness in a predetermined manner when exposed to the substance in an environment outside a human body.

4. The method of claim 3, wherein the surfactant-based biofilm has a thickness of about 200 Angstroms when not exposed to the substance in an environment outside a human body.

5. The method of claim 1, wherein the surfactant-based biofilm is exposed to saltwater to produce the reaction, which comprises adhesion of NaCl molecules to the surfactant-based biofilm.

6. The method of claim 5, wherein the surfactant-based biofilm includes salmon sperm DNA.

7. A sensor comprising a substrate with a surfactant-based biofilm thereon, the sensor located in an environment outside a human body, the surfactant-based biofilm characterized by its ability to react in a predetermined manner when exposed to a known substance in an environment outside a human body, the surfactant-based biofilm comprising a DPPC surfactant-based biofilm.

8. The sensor of claim 7, wherein the surfactant-based biofilm is characterized in that it has a predetermined thickness when not exposed to the known substance in an environment outside a human body and changes thickness in a predetermined manner when exposed to the known substance in an environment outside a human body.

9. The sensor of claim 8, wherein the surfactant-based biofilm is further characterized in that it will return substantially to its original predetermined thickness when exposure to the known substance in an environment outside a human body is discontinued.

10. The sensor of claim 8, wherein the surfactant-based biofilm has a thickness of about 200 Angstroms when not exposed to the known substance in an environment outside a human body.

11. A device for extracting salt from saltwater, comprising a substrate with a surfactant-based biofilm thereon, the surfactant-based biofilm comprising a DPPC surfactant-based biofilm that is characterized by its ability to react with saltwater to produce a reaction that causes a substantial portion of the NaCl molecules in the saltwater to adhere to the surfactant-based biofilm.

12. The device of claim 11, wherein the surfactant-based biofilm includes salmon sperm DNA.

13. The device of claim 12, wherein the surfactant-based biofilm has a thickness of about 300 Angstroms.

14. The device of claim 11, wherein the surfactant-based biofilm has a thickness of about 300 Angstroms.

15. A method of reacting a substance with a surfactant-based biofilm, comprising (a) providing a reactive structure comprising a substrate with a surfactant-based biofilm that is known to react with a substance in a predetermined manner when the surfactant-based biofilm is exposed to the substance, the surfactant-based biofilm comprising a DPPC surfactant-based biofilm; and (b) exposing the surfactant-based biofilm to the substance to produce the reaction with the substance in the predetermined manner;

wherein, the surfactant-based biofilm is exposed to a fluid containing the substance to produce the reaction, wherein the surfactant-based biofilm is characterized in that it has a thickness of about 200 Angstroms when not exposed to the substance, and wherein the surfactant-based biofilm is exposed to a substance in the fluid that includes any or all of the following genres of material to produce the reaction: a hydrocarbon that is harmful to a human lung, a hydrocarbon fuel, a biological and/or chemical warfare agent, a hydrocarbon-based solvent, an airborne metal that includes any or all of tungsten, arsenic and cobalt, a radioactive material, a gas containing nitric oxide, carbon dioxide or methane, a virus, engine oil vapors.

16. The method of claim 15, wherein the radioactive material includes 99m Tc DTPA; the hydrocarbon solvent includes any or all of ethanol, methanol, and acetone; the hydrocarbon fuel includes any or all of jet fuel, S-8 synthetic jet fuel, gasoline, diesel, kerosene; the biological and/or chemical warfare agent comprises any or all of ricin, sarin, anthrax, phosgene gas and mustard gas; and the virus includes Hong Kong 8/68.

17. The method of claim 6, wherein the surfactant-based biofilm has a thickness of about 300 Angstroms when not exposed to the saltwater.

18. A sensor comprising a substrate with a surfactant-based biofilm thereon, the surfactant-based biofilm layer characterized by its ability to react in a predetermined manner when exposed to a known substance, the surfactant-based biofilm comprising a DPPC surfactant-based biofilm, wherein the surfactant-based biofilm is characterized in that it has a predetermined thickness when not exposed to the known substance and changes thickness in a predetermined manner when exposed to the known substance, wherein the surfactant-based biofilm is further characterized in that it will return substantially to its original predetermined thickness when exposure to the known substance is discontinued, wherein the surfactant-based biofilm has a thickness of about 200 Angstroms when not exposed to the known substance, and wherein the surfactant-based biofilm in about a 200 Angstrom thickness has sensitivity such that it will change thickness in the predetermined manner when exposed to a substance that includes any or all of the following genres of material: a hydrocarbon that is harmful to a human lung, a hydrocarbon fuel, a biological and/or chemical warfare agent, a hydrocarbon-based solvent, an airborne metal that includes any or all of tungsten, arsenic and cobalt, a radioactive material, a gas containing nitric oxide, carbon dioxide or methane, a virus, engine oil vapors.

19. The sensor of claim 18, wherein the radioactive material includes 99m Tc DTPA; the hydrocarbon solvent includes any or all of ethanol, methanol, and acetone; the hydrocarbon fuel includes any or all of jet fuel, S-8 synthetic jet fuel, gasoline, diesel, kerosene; the biological and/or chemical warfare agent comprises any or all of ricin, sarin, anthrax, phosgene gas and mustard gas; and the virus includes Hong Kong 8/68.

* * * * *